United States Patent [19]

Borburgh et al.

[11] 4,305,014
[45] Dec. 8, 1981

[54] PIEZOELECTRIC ARRAY USING PARALLEL CONNECTED ELEMENTS TO FORM GROUPS WHICH GROUPS ARE $\approx \frac{1}{2}\lambda$ IN WIDTH

[75] Inventors: Jacobus Borburgh, Poxdorf; Ingmar Feigt, Erlangen, both of Fed. Rep. of Germany

[73] Assignee: Siemens Aktiengesellschaft, Berlin & Munich, Fed. Rep. of Germany

[21] Appl. No.: 49,898

[22] Filed: Jun. 19, 1979

[30] Foreign Application Priority Data

Jul. 5, 1978 [DE] Fed. Rep. of Germany ....... 2829570

[51] Int. Cl.³ ............................................ H01L 41/08
[52] U.S. Cl. .................................... 310/334; 310/367; 310/368
[58] Field of Search ................. 310/322, 327, 334–337, 310/367, 368; 367/155, 157; 128/660; 73/596, 625, 628, 632, 641, 642

[56] References Cited

U.S. PATENT DOCUMENTS

| 2,408,028 | 9/1946 | Batchelder | 310/368 X |
| 2,589,135 | 3/1952 | Rafuse et al. | 367/163 |
| 2,956,184 | 10/1960 | Pollack | 310/369 |
| 3,036,231 | 5/1962 | Henry | 310/327 X |
| 3,718,898 | 2/1973 | Cook et al. | 310/322 X |
| 3,827,115 | 8/1974 | Bom | 310/334 X |
| 3,971,962 | 7/1976 | Green | 310/322 |
| 4,101,795 | 7/1978 | Fukumoto et al. | 310/336 |
| 4,122,725 | 10/1978 | Thompson | 310/326 X |
| 4,156,158 | 5/1979 | Wilson et al. | 310/334 X |

FOREIGN PATENT DOCUMENTS 732890 8/1954 Fed. Rep. of Germany .
2521463 11/1975 Fed. Rep. of Germany .

Primary Examiner—Mark O. Budd
Attorney, Agent, or Firm—Hill, Van Santen, Steadman, Chiara & Simpson

[57] ABSTRACT

In an exemplary embodiment a transducer comb for an ultrasonic array or a compound scanner consists of a specifiable number of transducer elements joined together in a specific area formation, the width of each transducer element being smaller than its height. In the case of sonic heads of this type, given an optimum radiation or receiving power, respectively, the lateral resolution is to be significantly improved. This is achieved by a transducer element arrangement comprising a fine subdivision of the transducer elements in such a manner that the width of each individual transducer element lies markedly below half the wavelength ($\lambda/2$) of the radiated, or received, ultrasonic waves, whereby, however, within the arrangement, in each instance, always a specified number of transducer elements of the fine subdivision is combined into a group through parallel-connection. The total radiation/receiving surface, including the intermediate spaces, of such a group is to correspond to at least approximately the active area of an individual element of conventional transducer element arrangements. In spite of a relatively high loss due to the fine division of the transducer, at least the same radiation efficiency as in the case of conventional transducer arrangements results with the group interconnection, whereby, however, the echo response is virtually free of transverse vibrations.

10 Claims, 6 Drawing Figures

PIEZOELECTRIC ARRAY USING PARALLEL CONNECTED ELEMENTS TO FORM GROUPS WHICH GROUPS ARE ≃½λ IN WIDTH

BACKGROUND OF THE INVENTION

The invention relates to an ultrasonic head, in particular, a transducer comb for an ultrasonic array or a compound scanner, consisting of a specifiable number of transducer elements, which are joined together in a specific area formation, and whose width is smaller than the height.

The ultrasonic head can be a randomly-shaped scan head for B-scan or also for A-scan, or for a similar scan procedure. Thus, the present instance can also relate to an ultrasonic head for e.g. compound-scan. In a special application, the sonic head, however, is to be the transducer comb of an ultrasonic array.

A transducer comb for an ultrasonic array with the initially cited features is e.g. known from the article in "Electronic Sector Scanning for Ultrasonic Diagnosis" by J. C. Somer from the publication Ultrasonics, July 1968, pages 153 through 159. Specifically, it is a question here of a so-called phase-array for sector scanning. Accordingly, the segment-width of each individual transducer element lies in the range of half of the wavelength ($\lambda/2$) of the utilized ultrasonic vibrations, or, at most, only slightly below this. However, in the case of transducer combs of this type, the lateral resolution leaves something to be desired.

SUMMARY OF THE INVENTION

It is an object of the present invention to construct an ultrasonic head of the type initially cited which is significantly improved in the lateral resolution and which can be simultaneously introduced, with optimum radiation or receiving efficiency for all presently conventional scan procedures; thus for example, compound scan, linear array scan, or also as a phased array for section scan.

In accordance with the invention the object is solved by a transducer element arrangement with a fine subdivision of the transducer elements in such a manner that the width of each individual transducer element, at least at one location, lies markedly below half the wavelength ($\lambda/2$) of the radiated, or received, respectively, ultrasonic waves, whereby, within the transducer elements of the fine subdivision are, in each instance, combined, by means of parallel-connection, into groups whose total radiation or receiving surface, respectively, including the intermediate spaces, preferably corresponds to at least approximately the active area of an individual element of a conventional transducer element arrangement.

A transducer element arrangement finely subdivided in accordance with the invention guarantees, in the group interconnection, in spite of relatively high division losses (intermediate spaces, for example, amount of 20% of the active surface) at least the same radiation or receiving power, respectively, as a conventional transducer element arrangement, whereby, however, an echo response results which is always virtually free of transverse vibrations. Thus, with an optimum radiation or receiving power, respectively, the lateral resolution is likewise optimum.

In an advantageous embodiment of the invention, the width of each individual transducer elements of a group should be at least smaller than $\lambda/4$. The intermediate spaces should not substantially exceed gap widths on the order of magnitude of 1/5 of the respective transducer element width. The parallel-connection into group-contacting of the individual transducer elements within the group. There is then allocated to each group-contacting an individual signal line for activating (or operating) the group.

Further details of the invention will be apparent from the following description of an exemplary embodiment on the basis of the accompanying sheets of drawings in conjunction with the sub-claims; and other objects, features and advantages will be apparent from this detailed disclosure and from the appended claims.

DETAILED DESCRIPTION

Figure 1:
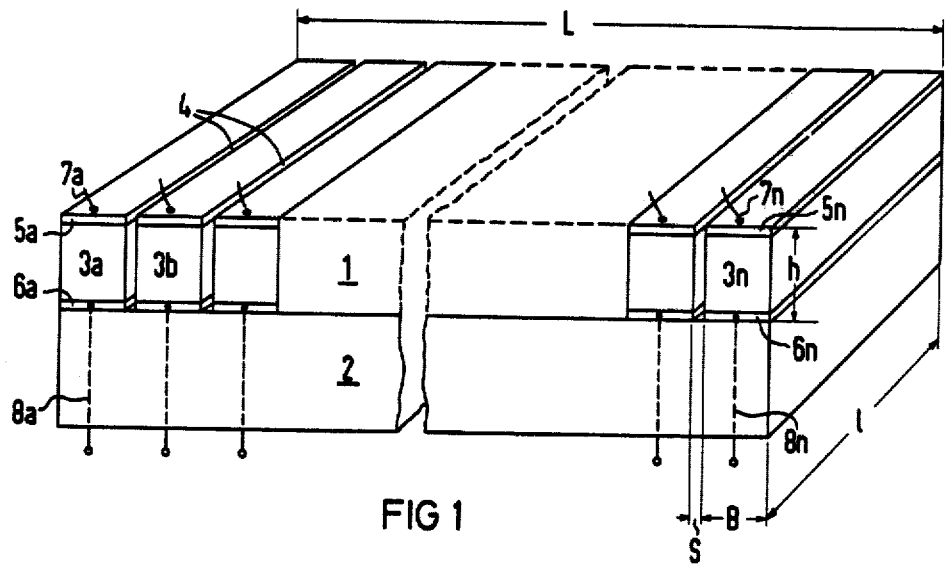
FIG. 1 illustrates an ultrasonic array with a conventional transducer comb.

On principle, the ultrasonic array of FIG. 1 can correspond to that of the initially cited Somer article. It then comprises a transducer comb 1 with a carrier section 2 e.g. consisting of epoxide resin. The transducer comprises a plurality of transducer elements $3a$ through $3n$ consisting of piezoelectric material (for example, consisting of lead-zirconate-titanate). The individual transducer elements $3a$ through $3n$ are arranged next to one another on the carrier section 2 with a spacing therebetween of (S). According to the Somer-article, the gaps 4 between the individual transducer elements are filled with spacing pieces consisting of epoxide resin. Of course, however, they can also remain unfilled in the form of gaps (for example, according to FIG. 1). Each individual transducer element $3a$ through $3n$ manifests an electrical contacting $5a$ through $5n$ allocated to it on the upper side, and $6a$ through $6n$ on the underside (silver coatings) for the connection of operating (or control) lines $7a$ through $7n$, and $8a$ through $8n$, respectively. The number of transducer elements lies e.g. in the range of 125. The overall length of the ultrasonic array is designated by (L) (L equals approximately 10 cm). The length of the individual transducer elements $3a$ through $3n$ amounts to (1), their height is indicated by (h), and the width amounts to (B). The gap width of the gaps 4 possesses the value (S). The transducer element width lies in the range of half ($\lambda/2$) of the wavelength of the utilized ultrasonic vibrations, or at most, slightly therebelow. In accordance with the initial requirements, the height (h) is greater than the width (B) of each individual transducer element $3a$ through $3n$.

As previously mentioned, the lateral resolution of such an ultrasonic array, such as is illustrated for example in FIG. 1, is not yet optimum. It becomes optimum, in the case of at least the same radiation or receiving power, respectively, with the exemplary embodiment of FIG. 2 and also with the exemplary embodiments of FIGS. 3 through 6, respectively.

Figure 2:
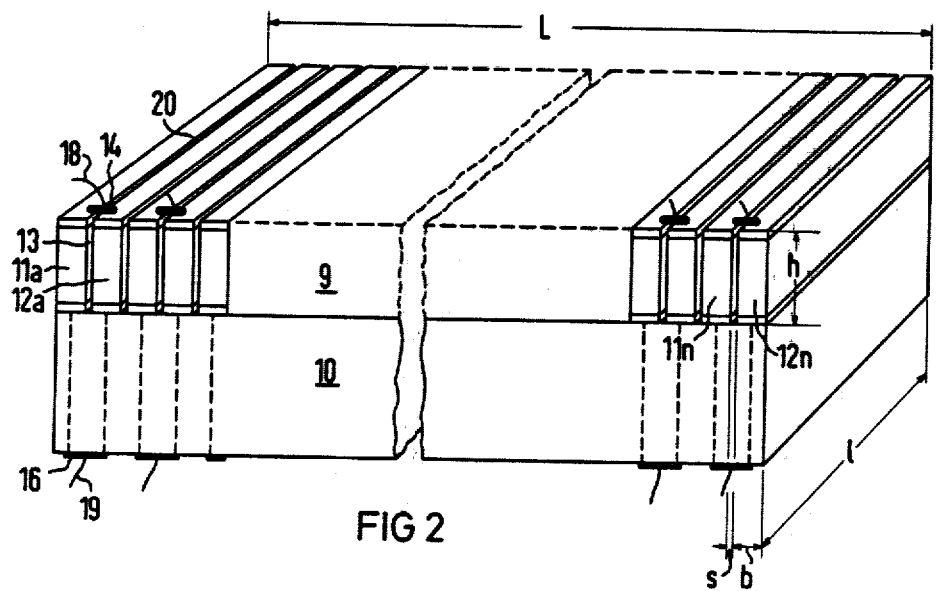
FIG. 2 illustrates an ultrasonic array with a transducer comb in fine subdivision in accordance with the invention.

The ultrasonic array of FIG. 2 comprises a transducer comb 9 which is supported on a carrier 10 (e.g. again epoxide resin). In contrast with the transducer comb 1 of the array of FIG. 1, however, the transducer comb 9 of the array of FIG. 2 is finely subdivided. In the illustrated sample embodiment of FIG. 2, there are thus now groups of two transducer elements 11a, 12a through 11n, 12n, instead of single transducer elements 3a through 3n according to FIG. 1. The individual elements 11a, 12a through 11n, 12n, each manifest a width (b) which possesses less than half the width (B) of a transducer element 3a through 3n of the array of FIG. 1. The transducer element width (b) of the transducer elements 11a, 12a, and 11n through 12n, in the fine subdivision of the exemplary embodiment of FIG. 2, is thus smaller than ($\lambda/4$) and correspondingly also substantially smaller than half ($\lambda/2$) of the wavelength of the utilized ultrasonic vibrations. Of the elements 11a, 12a through 11n, 12n of the fine subdivision, however, in each instance always two adjacent elements are combined into a group 13. The group-wide integration proceeds by means of soldering locations 14 on the upper side (radiation surface) and 16 on the underside. Each group-contacting manifests its own control line connection 18 on the radiation surface and 19 on the underside. Within such a group 13, the total radiation/receiving surface which is commonly formed by two transducer elements 11a, 12a through 11n, 12n, respectively, including the intermediate space formed by gap 20, is then approximately equally as great in area as the active surface of an individual transducer element 3a through 3n of the ultrasonic array of FIG. 1. In spite of the relatively high gap loss (the gap loss amounts to approximately 20% of the active surface area), there results, for each of the individual groups 13 of the transducer comb 9, at least the same radiation or receiving power, respectively, as for each of the transducer elements 3a through 3n of FIG. 1, whereby, however, the lateral resolution in significantly improved. If one compares active surfaces, then there results, in the case of the fine—array of FIG. 2, an echo response which is even higher by approximately four decibels (+4 dB) than in the case of the conventional array of FIG. 1.

In the case of a sample embodiment used in practice, the ultrasonic array of FIG. 2 comprises, given an ultrasonic frequency of $f=2.25$ MHz, a total of 256 individual transducers 11, 12a through 11n, 12n. The width of each individual transducer amounts to approximately 0.26 millimeters (b=0.26 mm). The height of the elements amounts to approximately 0.7 millimeter (h=0.7 mm), and the length amounts to approximately eleven millimeters (l=11 mm). Given a gap width on the order of magnitude of 0.05 to 0.06 millimeters (s=0.05 to 0.06 mm), upon integrating a total of two transducer elements into a group, there thus results an overall group width of approximately 0.57 mm, whereby the individual groups are again mutually separated along the transducer comb 9 by gap widths which are again on the order of magnitude of 0.05 to 0.06 millimeter (s=0.05 to 0.06 mm).

The fine subdivision of the transducer comb according to the array of FIG. 2 can e.g. be carried out by a sawing technique by means of a gate saw (Gattersäge in German), or also by means of a cutting beam; for example, a laser beam or an ultrasonic-cutting beam. The application of the stacking technique is thin sheets, LSI photoresist technique and etching technique, or also the sintering technique in rod shape is likewise possible.

Figure 3:
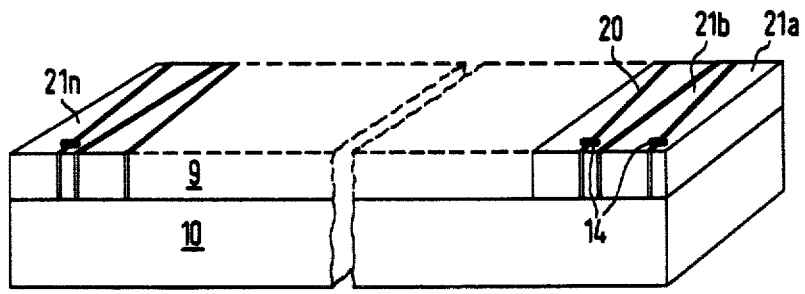
FIG. 3 illustrates a subdivision shape in trapezoidal oblique steps over the length of a transducer strip.
Figures 4, 5:
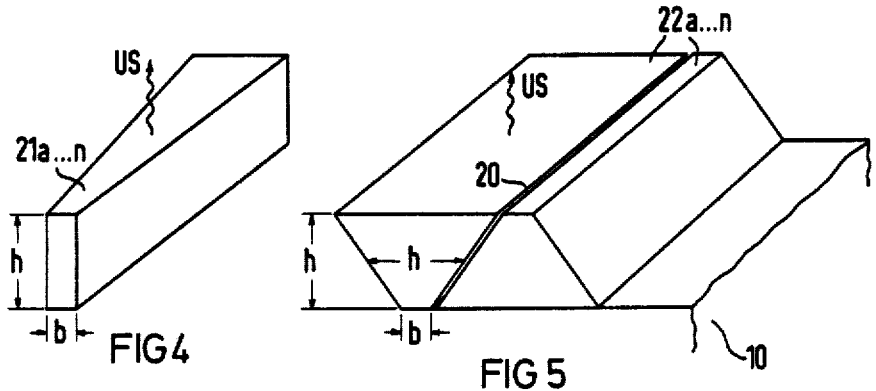
FIG. 4 illustrates an individual segment of the subdivision according to FIG. 3 in an enlargement.
FIG. 5 illustrates a subdivision shape in trapezoidal oblique (or inclined) steps over the height of the transducer element strip.

The transducer elements 11a, 12a through 11n, 12n, can have the rod-shape illustrated in FIG. 2 with width (b) which remains constant over the transducer length (l) and transducer height (h). However, other geometric configurations are likewise possible; for example, the trapezoidal shape according to height (h) and/or length (l), whereby, however, the width (b), at least at one location of the individual transducer element, should satisfy the requirments of the invention. Exemplary embodiments of this type are illustrated by FIGS. 3 through 5 with transducer element shapes as shown at 21a through 21n or 22a through 22n.

The exemplary embodiment of FIG. 2 functions with two individual elements 11a, 12a etc. through 11n, 12n per group. Of course, also more than only two—for example, three, four, or more individual elements—can be interconnected into a transducer group. The individual elements can then be subdivided in a yet finer fashion so that, for example, a width condition considerably smaller than $\lambda/4$ and thus very much smaller than $\lambda/2$ results. The overall width of each transucer group can then again be approximately $\lambda/2$. Such an ultrasonic array is then again particularly suited for application for sector scanning. However, the overall width of the transducer group can likewise be greater than $\lambda/2$. Such embodiments are utilized e.g. in the case of linear arrays. All these embodiment modifications are, of course, intended to fall within the protective scope of the invention.

Figure 6:
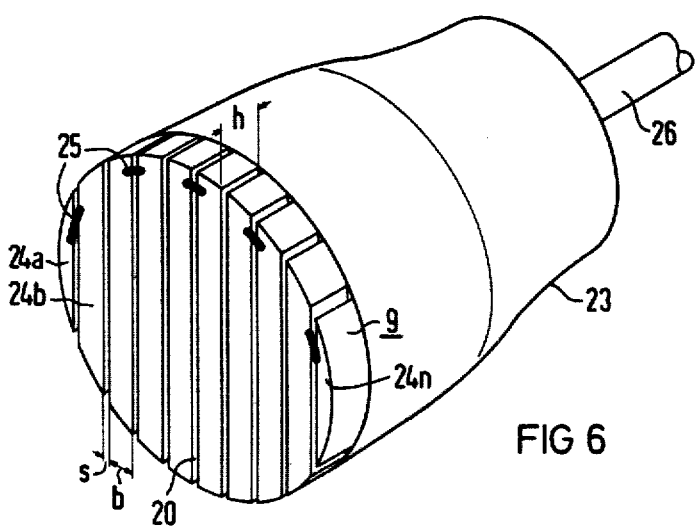
FIG. 6 illustrates an ultrasonic head for compound scan which is subdivided in accordance with the invention.

The corresponding also applies to the embodiment of FIG. 6, which illustrates a sonic head 23, particularly for ultrasonic compound scan. The ultrasonic transducer elements 24a through 24n again form a comb-shaped radiation and/or receiving surface, respectively, which, however, is now round, with a group connection 25 according to the teaching of the invention. Reference numeral 26 designates a connection cable for the sonic head. The rod embodiment of FIG. 6, as required, can be replaced by a mosaic or matrix embodiment; for example, through formation of transverse gaps. The same, of course, also applies to the array—comb embodiments of FIGS. 1 through 5.

It will be apparent that many modifications and variations may be effected without departing from the scope of the novel concepts and teachings of the present invention.

We claim as our invention:

1. An ultrasonic head, especially for operation as an ultrasonic array or a compound scanner, comprising a specifiable number of transducer elements joined together in a specific surface configuration, the width of each transducer element being smaller than the height, characterized by a transducer element arrangement (9) with a fine subdivision of the transducer elements (11a, 12a through 11n, 12n; 21a through 21n; 22a through 22n; 24a through 24n) in such a manner that the width (b) of each individual transducer element, at least at one location, lies substantially below half the wavelength ($\lambda/2$) of the radiated, or received ultrasonic waves, the transducer element arrangement (9), in each instance, having successive sets of the transducer elements of the fine subdivision electrically combined into respective groups (13) through electrical parallel-connection; the total radiation or receiving active surface including the intermediate spaces (20) of each of said groups having a width equal to at least about one-half the wavelength ($\lambda/2$), each set of transducer elements comprising at least two of said transducer elements and having electrical conductors (14, 16; 25) directly and permanently interconnecting said set of transducer elements for joint transducing operation.

2. An ultrasonic head according to claim 1, characterized in that the width (b) of each individual transducer element of a group (13) is at least less than $\lambda/4$.

3. An ultrasonic head according to claim 1, characterized in that the intermediate spaces manifest gap widths (s) on the order of magnitude of a maximum of 1/5 of the respective transducer element width (b).

4. An ultrasonic head according to claim 1, characterized in that the parallel connection into groups (13) occurs by means of common group-contacting (14, 16; 25) of the individual transducer elements within the group.

5. An ultrasonic head according to claim 4, characterized in that there is allocated to each group-contacting (14, 16; 25) a separate signal line (18, 19) for the purpose of operating the group (13).

6. Ultrasonic head according to claim 1, with the transducer groups (13) being formed of rod shaped transducer elements (11a, 12a through 11n, 12n) each having a width (b) which is constant over the element length (l) and having an element height (h), and having a width (b) which is smaller than one-half the wavelength ($\lambda/2$).

7. An ultrasonic head according to claim 1, with the transducer groups being formed of transducer elements (21a through 21n) with a constant element height (h), but with a width (b) increasing over the element length (l) from a low value which is smaller than $\lambda/2$ to a maximum value which maximum value lies in the range of at least about $\lambda/2$.

8. An ultrasonic head according to claim 1, with the transducer element groups being formed of transducer elements (22a through 22n) with a constant element length (l), and a width (b) increasing over the element height (h) from a low value smaller than $\lambda/2$ to a maximum value which maximum value lies in the range of at least about $\lambda/2$.

9. An ultrasonic head according to claim 1, with the transducer element groups having a length less than the length of the total active surface to provide a subdivided surface arrangement with longitudinal and transverse gaps between the groups.

10. An ultrasonic head according to claim 1, characterized by the transducer element groups being arranged to define a round transducer active surface.

* * * * *